United States Patent
Haverinen et al.

(10) Patent No.: US 10,893,833 B2
(45) Date of Patent: *Jan. 19, 2021

(54) WEARABLE ELECTRONIC DEVICE AND METHOD FOR MANUFACTURING THEREOF

(71) Applicant: Oura Health Oy, Oulu (FI)

(72) Inventors: Teemu Haverinen, Oulu (FI); Marko Kelloniemi, Oulu (FI); Tomi Hautala, Oulu (FI); Markku Koskela, Oulu (FI); Kari Kivelä, Helsinki (FI)

(73) Assignee: Oura Health Oy, Oulu (FI)

( * ) Notice: Subject to any disclaimer, the term of this patent is extended or adjusted under 35 U.S.C. 154(b) by 54 days.

This patent is subject to a terminal disclaimer.

(21) Appl. No.: 15/835,573

(22) Filed: Dec. 8, 2017

(65) Prior Publication Data

US 2018/0103902 A1  Apr. 19, 2018

Related U.S. Application Data

(63) Continuation of application No. 14/826,360, filed on Aug. 14, 2015, now Pat. No. 9,861,314.

(51) Int. Cl.
*A61B 5/00* (2006.01)
*A61B 5/01* (2006.01)
*A61B 5/024* (2006.01)
*G06F 1/16* (2006.01)
*B28B 1/24* (2006.01)

(52) U.S. Cl.
CPC .............. *A61B 5/6801* (2013.01); *A61B 5/01* (2013.01); *A61B 5/681* (2013.01); *A61B 5/6826* (2013.01); *G06F 1/163* (2013.01); *A61B 5/02416* (2013.01); *A61B 2562/00* (2013.01); *A61B 2562/12* (2013.01); *B28B 1/24* (2013.01)

(58) Field of Classification Search
CPC ..... A61B 5/6801; A61B 5/6826; A61B 5/681; A61B 5/01; A61B 2562/12; A61B 5/02416; A61B 2562/00; G06F 1/163; B28B 1/24

See application file for complete search history.

(56) References Cited

U.S. PATENT DOCUMENTS

| | | | | |
|---|---|---|---|---|
| 6,553,667 | B1 * | 4/2003 | West | A44C 9/00 164/80 |
| 9,582,034 | B2 * | 2/2017 | von Badinski | G06K 9/00885 |
| 2013/0287622 | A1 * | 10/2013 | Hoffman | A44C 27/003 420/436 |
| 2015/0220109 | A1 * | 8/2015 | von Badinski | A61B 5/021 340/539.12 |
| 2016/0058375 | A1 * | 3/2016 | Rothkopf | G06F 1/1643 600/301 |
| 2016/0070393 | A1 * | 3/2016 | Sharma | G06F 1/163 345/174 |

(Continued)

*Primary Examiner* — Anthony M Haughton
(74) *Attorney, Agent, or Firm* — Ziegler IP Law Group, LLC (57) ABSTRACT

A wearable electronic device includes a body part made of a non-ceramic material, having an inner surface and an outer surface, wherein at least one cavity having a depth is arranged on the inner surface of the body part, an electronic part arranged in the at least one cavity, which electronic part has a thickness that is less than the depth of the at least one cavity, and a coating made of a moldable filler material on the inner surface of the body part, covering the electronic part and the at least one cavity.

12 Claims, 6 Drawing Sheets

(56) References Cited

U.S. PATENT DOCUMENTS

2016/0116941 A1* 4/2016 Kuwabara ............... G06F 1/163
                                                    361/679.03
2016/0139702 A1* 5/2016 Franklin ................. G06F 3/044
                                                    345/174
2016/0274621 A1* 9/2016 Meyer ................... B29C 39/021
2016/0287102 A1* 10/2016 Saponas ............. A61B 5/02233

* cited by examiner

WEARABLE ELECTRONIC DEVICE AND METHOD FOR MANUFACTURING THEREOF

CROSS-REFERENCE TO RELATED APPLICATION

This application is a continuation of, claims priority to and the benefit of, U.S. patent application Ser. No. 14/826,360, filed 14 Aug. 2015, status pending, the disclosure of which is incorporated herein by reference in its entirety.

TECHNICAL FIELD

The present disclosure relates generally to a wearable electronic device; and more specifically, to a wearable electronic device for analysing and processing of biological signals and a method for manufacturing such wearable electronic device.

BACKGROUND

Recent consumer's interest in personal health has led to a variety of personal health monitoring devices being offered in the market. For example, wearable electronic devices for monitoring personal health are well known in the art. The wearable electronic devices are measurement devices that can be worn on finger, wrist or any other body part. Generally, such devices include electronic elements, such as flexible printed circuit board, processor, sensor, battery and the like, which enable measurement and/or analysis of different physiological parameters, such as heart beat, corresponding to a user.

Typically, these wearable devices are designed in a way such that it is water proof and provides a smooth skin contact to the wearer. A known way to make these devices waterproof is to have a two part cover, for the electronic elements, which are connected to each other for enclosing the electronic elements therewithin. For example, the two parts can be connected together using attachment means, such as screws or clips. Further, a sealing material, such as o-ring, is provided between the two parts while connecting the two parts for making the connection water proof. However, such water proof arrangement for the wearable devices makes their structure configuration complex due to the involvement of various components such as the first cover, the second cover, the o-ring and the screws. Further, this may lead to manufacturing defects since the components are made with small tolerances. For example, the wearable electronic devices may be subjected to manufacturing errors, such as too much tightening or loosening of one or more screws, which may lead to non-waterproof sealant. Moreover, an inner surface (contacting the user's skin) of such devices should be free from any cavity or depression (for example, grooves for screws) which may get deposited with dirt. Additionally, the inner surface should be smooth and provide good adherence with the user's skin when worn in the finger, wrist or any other body part.

Therefore, in light of the foregoing discussion, there exists a need to overcome the aforementioned drawbacks of the conventional wearable electronic device.

SUMMARY

The present disclosure seeks to provide a wearable electronic device, particularly, for analysing and processing of biological signals.

The present disclosure also seeks to provide a method for manufacturing a wearable electronic device for analysing and processing of biological signals.

In one aspect, an embodiment of the present disclosure provides a wearable electronic device comprising:

a molded body part made of a moldable ceramic material, having an inner surface and an outer surface, wherein at least one cavity having a depth is arranged on the inner surface of the body part, an electronic part arranged in said cavity, which electronic part has a thickness that is less than the depth of the cavity, and a coating made of a moldable filler material on the inner surface of the body part, covering the electronic part and the cavity.

In another aspect, an embodiment of the present disclosure provides a method for manufacturing a wearable electronic device. The method comprises the steps of:

molding a body part using a moldable ceramic material, wherein a mold is such that at least one cavity is formed on an inner surface of the body part, arranging an electronic part in said cavity, and coating the inner surface of the body part to form the coating including covering the electronic part.

Embodiments of the present disclosure substantially eliminate or at least partially address the aforementioned problems in the prior art, and provides a wearable electronic device having a simple structure configuration and efficient waterproofing.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a wearable electronic device. The wearable electronic device comprises a molded body part made of a moldable ceramic material, having an inner surface and an outer surface, wherein at least one cavity having a depth is arranged on the inner surface of the body part, an electronic part arranged in said cavity, which electronic part has a thickness that is less than the depth of the cavity, and a coating made of an epoxy material on the inner surface of the body part, covering the electronic part and the cavity.

In an embodiment, the wearable electronic device is operable to measure different physiological parameters corresponding to a user, such as blood volume pulse, to determine a heart rate of the user. In an example, the heart rate is determined by measuring PPG (photoplethysmogram) from the blood volume pulse. The PPG can be measured or generated using optical electronics, particularly using principle of transmittance or reflectance of light. Additionally, the wearable electronic device is also operable to measure stress of the user.

In an embodiment, the wearable electronic device is a ring that can be worn by a user in a finger. For example, the wearable electronic device is sized to be suitably worn on a finger, such as an index finger, of the user. Further, it may be available in a variety of sizes for accommodating various finger sizes. In another embodiment, the wearable electronic device may be a wrist band that may be worn on a wrist of the user. In such instance, it may be evident to those skilled in the art that a size of the wearable electronic device should be large enough to be suitably worn at the wrist of the user.

The wearable electronic device comprises a molded body part made of a moldable ceramic material. As mentioned herein, the wearable electronic device is a ring, therefore the molded body part may be configured to have a central portion and a loop integral with the central portion for a ring structure. Alternatively, the central portion and the loop can be formed separately and later joined together to form the body part.

In an embodiment, the moldable ceramic material is selected from a group consisting of zirconia, zirconium, aluminum nitride, aluminum oxide, Boron carbide, silicon carbide, silicon nitride, titanium diboride and yttrium oxide. Alternatively, non-ceramic material, such as plastic, metal (such as titanium, steel, platinum, gold, palladium, silver or bronze or a gold based alloys), rubber or any combination thereof may be used for forming the molded body part.

The molded body part includes the inner surface, the outer surface and at least one cavity having the depth arranged on the inner surface of the body part. The inner surface contacts the skin of the user, whereas the outer surface is opposite to the inner surface and externally visible. The at least one cavity is made during the molding of the body part. Alternatively it is possible form the cavities to body part by cutting or milling. Further the outer surface can be formed or finalised by milling or polishing up or other metallic workshop methods.

In an embodiment, the at least one cavity of the molded body part includes two cavities, such as a first cavity and a second cavity, which are formed on the inner surface of the molded body part. Further, the first cavity and the second cavity are connected with each other. Moreover, the first cavity resides in the central portion of the molded body part and the second cavity runs along the loop and is connected to the first cavity. In an embodiment, a depth of the first cavity is slightly more than a depth of the second cavity. For example, if the second cavity has a depth of about 1 mm, then depth of the first cavity would be slightly more than 1 mm. Also, shapes of the two cavities may vary depending upon shapes of the central portion and the loop.

The wearable electronic device further comprises the electronic part arranged in the cavity, which electronic part has a thickness that is less than the depth of the cavity. Specifically, the cavity is dimensioned to have the depth which is sufficient to allow the electronic part to be fully placed inside the cavity, and an unfilled space still remains when the electronic part is fully placed inside the cavity.

In an embodiment, the electronic part comprises a battery and a support on which other components of the electronic part are arranged. For example, the other components of the electronic part (arranged on the support) may include but not limited to an infrared transmitter, a microcontroller, a radio frequency transceiver, a temperature sensor and an infrared receiver.

In an embodiment, the support also comprises means for charging the battery, such as the charging pads (or charging pins). In an embodiment, there may be two or more charging pads arranged, for example on the inner surface of the support. In an embodiment, the support is a flexible printed circuit board (PCB), for example, a flexible plastic substrate made of polyimide, PEEK (a transparent conductive polyester film), polyester or a combination thereof.

In an embodiment, the electronic part includes a first part and a second part. For example, the battery and a portion of the support (flexible PCB) on which the microcontroller is arranged (or mounted) constitute the first part of the electronic part. Further, a remaining portion of the support and the other components of the electronic part arranged on the remaining portion constitute the second part of the electronic part. In an embodiment, the first part and the second part are connected to each other using electrical wires. For example, the battery may be electrically coupled to the support (particularly to the microcontroller) using the electrical wires. As mentioned above, the electronic part is arranged in the cavity. For example, the first part of the electronic part is arranged in the first cavity and the second part of the electronic part is arranged in the second cavity.

In an embodiment, the electronic part is attached to the cavity by an attachment means arranged at a bottom of the cavity. The attachment means is selected from a group consisting of a sticker, a tape, glue, and an attachment structure made in the molded body part. In an example, a sticker (or a stick foam tape) may be arranged at a bottom of the first cavity and the battery may be adhered to central portion and inside the first cavity with the help of the sticker. Similarly, another sticker (or a stick foam tape) may be arranged at a bottom of the second cavity (or on the support, i.e. flexible PCB) such that the support may be adhered to loop and within the second cavity with another sticker.

In one embodiment, the electronic part is aligned in proper position with respect to the molded body part using an assembly guiding element (the attachment structure made in the molded body part). Specifically, the second part can be aligned with respect to the second cavity by using the assembly guiding element. In an example, the assembly guiding element is a protruding part, such as a tab or a spike, configured on the inner surface, preferably, on the loop. In an embodiment, there is a single assembly guiding element configured on the inner surface of the loop. Alternatively, there can be more than one assembly guiding elements arranged on the inner surface of the loop. Typically, the support includes at least one hole corresponding to the assembly guiding element for receiving the assembly guiding element therethrough and aligning the electronic part (particularly the support) with respect to the molded body part (particularly to the second cavity).

The wearable electronic device further comprises a coating made of an moldable filler material on the inner surface of the body part, covering the electronic part and the cavity. For example, the moldable filler material is filled in the cavity embedded with the electronic part. Specifically, the moldable filler material is filled to cover the unfilled space that still remains, when the first cavity and the second cavity respectively receive the first part and the second part of the electronic part therein. Therefore, the coating made of the moldable filler material sealingly covers for electronic part and fills the remaining space of the cavity arranged on the inner surface of the molded body part.

In an embodiment, the moldable filler material is selected from a group consisting of at least epoxy material, Polyethylene, Polyurethane, low temperature moldable material (low temperature refers to below 100 degrees of Celsius in order not to cause too high temperatures for the electronics parts), Loctite M-31CL, alpha-epoxy, EpoxAcast® 650, Bisphenol S epoxy resin, Novolac epoxy resin, Aliphatic epoxy resin and Glycidylamine epoxy resin.

In an embodiment, the moldable filler material comprises optionally an ink, which ink increases value of transmitted infrared light intensity divided by transmitted light intensity. In other words relative mount of infrared light which can pass thru the moldable filler material with the ink compared to amount of visible light which can pass thru the moldable filler material is higher when the ink is used in comparison to no ink. As an example, if the moldable filler material is selected as epoxy material, the epoxy material is a mixture of an epoxy resin and a colorant (i.e. the ink). In an example, the ink is an inkjet ink, such as a Magic Black ink. Further, the moldable filler material comprising the ink is arranged to cover at least area other than the IR transmitter and the IR receiver within the cavity. The moldable filler material comprising the ink can cover also IR transmitter and the IR receiver.

In another aspect, an embodiment of the present disclosure provides a method for manufacturing the wearable electronic device. The method comprises steps of molding a body part using a moldable ceramic material, wherein a mold is such that at least one cavity is formed on an inner surface of the body part; arranging an electronic part in said cavity; and coating the inner surface of the body part by applying an epoxy resin on the surface and curing the resin to form an epoxy coating, including covering the electronic part.

In an embodiment, the molding of the body part is done with the use of a mold. The mold essentially comprises a first part and a second part conforming to the central portion and the loop of the molded body part, such that when the moldable ceramic material is injected into the mold, the molded body part with the central portion and the loop is formed.

In an embodiment, the molded body part is formed using a ceramic injection molding (CIM) technique. As an example of CIM technique zirconia is injected in a mold and then further sintered in temperatures range of about 1300-1550 degrees Celcius.

In addition a ceramic molding technique such as slip casting, ceramic shell casting and technical ceramics can be used. Typically, the ceramic molding technique is performed at a temperature range of about 1500-2500 degree Celsius depending on the moldable ceramic material used. For example, if the moldable ceramic material used is zirconium, the molding is performed at a temperature of about 1855 degree Celsius and similarly, if the moldable ceramic material used is aluminum nitride, the molding is performed at a temperature of about 2200 degree Celsius.

Alternatively, the molded body part (when formed using non-ceramic material) can be molded using a molding technique, such as compression molding, extrusion molding, injection molding and rotational molding. In another embodiment, the body part can be made from other manufacturing techniques, such as forming, machining, three dimensional (3D) printing and the like. In one embodiment, the non-ceramic material of the molded body part is a machinable material. In one embodiment, the non-ceramic material is a machinable titanium material. In a further embodiment, the non-ceramic material is a machinable metallic material comprising one or more of titanium, steel, platinum, gold, palladium, silver or bronze or a gold based alloys. Further the molded body part can be formed for example by using ultraviolent (UV) based curing method where ceramic material such as alumina (Al2O3) is mixed in curable solution and then illuminated with high intensity ultraviolent lamps (220-450 nm) for sufficient times.

The mold (used for molded body part) is such that at least one cavity is formed on an inner surface of the body part. Specifically, the mold used for forming the body part is such that at least one cavity is formed on the inner surface of the molded body part. Specifically, the molded body part is such that two cavities, a first cavity and a second cavity, are formed on the inner surface of the body part. Further, the first cavity and the second cavity are in connection with each other.

The electronic part is arranged in the cavity thereafter. In an embodiment, the step of arranging the electronic part in the cavity is carried out by arranging the battery in the first cavity, connecting the battery to the support and arranging the support in the second cavity. Initially, the step involves arranging the first part of the electronic part in the first cavity. In an embodiment, the electronic part (particularly, the first part) is arranged in the first cavity using the attachment means arranged on bottom of the first cavity. Specifically, the first part (i.e. battery and the portion of the support having the microcontroller mounted thereon) is first set in the first cavity. More specifically, first an orientation of the support is matched with an orientation of an assembly guiding element. In an embodiment, a sticker (or a stick foam tape) is removed with its covers and initially pasted to the central portion (i.e. inside the first cavity), thereafter a surface of the battery is located against the sticker to fix the battery into the first cavity. For example, the battery is pressed by a finger for about 10 seconds to properly fix the battery to the first cavity. Thereafter, the portion of the support having comparatively a larger width (i.e. a width of the central portion) and the microcontroller mounted thereon is also allowed to be placed on top of the battery.

In an embodiment, the battery is connected to the support. For example, the battery is connected to the support using electrical wires. Specifically, the battery is physically and electrically coupled to the support (particularly to the microcontroller) using the electrical wires, for example by soldering. In an embodiment, the battery is connected to the support with wires prior to the placement of the battery into the first cavity. Alternatively, the battery is connected to the support with the wires after the placement of the battery into the first cavity.

The support is thereafter arranged in the second cavity. Specifically, a remaining portion of the support (having a width of about the loop) along with other components of the electronic part arranged or mounted thereon is arranged in the second cavity. The support is made of a flexible material (as discussed above), therefore the support is first slightly bend downwards and rotated so that it gets accommodated easily inside the second cavity of the molded body part. Further, in an embodiment, a sticker (or stick foam tape) is removed with its covers and pasted to a side (that will face the inner surface of the loop) of the support. The use of sticker for arranging the support inside the second cavity enables in proper adherence of the support with the loop of the molded body part.

In another embodiment, the step of arranging the electronic part (the support) in the cavity is further carried out using at least one assembly guiding element, such a tab or spike. Specifically, the support includes at least one hole conforming to the at least one assembly guiding element for receiving the assembly guiding element therethrough. For example, the molded body part includes one assembly guiding element configured on inner surface of the one side of the loop, alternatively the molded body part may include two or more assembly guiding elements configured on inner surface of the both sides of the loop. The assembly guiding element fits into (or receives) the hole, thereby aligning the electronic part in proper position with respect to the cavity of the molded body part.

In an embodiment, in order to ensure a proper alignment of the electronic part into the cavity of molded body part, a check is made to ensure that the guiding element properly fits into (or receives) the hole. For example, a check is made to ensure that the whole electronic part, i.e. the battery and the support, is fully inside the molded body part. Additionally, after the support accommodation into the second cavity, another check is made to ensure that the battery cable (the electrical wires) goes between the battery and the molded body part.

In another embodiment, the support (particularly, the infrared transmitter and/or the infrared receiver mounted thereon) may not fully lie inside the cavity. For example, the infrared transmitter and receiver may be arranged in such a way that the infrared transmitter and receiver form bulges (or extension) emerging out from the support. The infrared transmitter and receiver accordingly can efficiently contact (or papule) the skin of the user when the user wears the wearable electronic device. Alternatively, the infrared transmitter and/or the infrared receiver may be fully accommodated inside the second cavity.

According to an embodiment, the proper fitting of the electronic part within the cavity ensures that there is unfilled space or volume for an epoxy material coating.

In an embodiment, the moldable filler material coating is made on the inner surface of the molded body part using a molding stand. The molding stand includes a base, a channel arranged on the base, and an elongate member extending from the base. The channel and the elongate member are configured to conform to a shape of the molded body part. Specifically, the channel is configured to conform to a thickness of the molded body part, whereas the elongate member is configured to conform to a circumference (or diameter) of the loop of the elongate member. This allows the elongate member to firmly fit over the molding stand. The elongate member further includes an opening and a recess surrounding the opening. The molding stand may be made of a material selected from a group consisting of fibers and fillers, latex, polyurethane rubber, thermosetting plastic and silicone rubber. Alternatively, the molding stand may be made of a material which is highly heat resilient and hard.

In an embodiment, the molding stand further includes jig pads at its one side, which helps in accurately placing the molded body part (with the electronic part arranged therein) onto the molding stand. For example, charging pads of the support (arranged inside of the molded body part) are set against these jig pads and the molded body part is assembled slightly tilted towards the molding stand. Further, the molded body part (with the electronic part arranged therein) is placed onto the molding stand in such a way that contact of the electronics (embedded in the support) with an edge of the molding stand is avoided. Furthermore, the molded body part is placed against a bottom surface of the base of the molding stand by receiving the molded body part into the channel, thereby having a centre of the molded body part aligned with a centre of the molding stand.

In one embodiment, the moldable filler material comprises an ink to make the modlable filler material appear dark or black for the user. The ink is selected in such a way that it allows infrared light to pass thru relatively better than visible light. The moldable filler material can be arranged thus to cover at the infrared transmitter and the infrared receiver. For example, if moldable filler material is selected to be epoxy material, the epoxy material is made by mixing the epoxy resin and the ink. Specifically, the mixture is prepared by adding a small amount of the ink (for example, in a range of 0.05 g-0.1 g) to the epoxy resin (for example, 30-70 ml) and mixing the epoxy resin and the ink uniformly with a stirrer.

The mixture is then heated in an oven at a temperature of about 60 degree Celsius for about 20 minutes for uniformly mixing of the epoxy resin and the ink. Further, the mixture is again stirred for further mixing and stored in a tube. The tube may be closed using a cover, which may be prick or pierce with a needle for allowing air to escape from within the tube. More, the mixture may be further heated before dispensing (or pouring) into the molding stand.

In an embodiment, flowable (or heated) mixture is poured into the opening of the elongate member of the molding stand (with the molded body part along with the electronic part mounted thereon). For example, the mixture is added into the molding stand from a dispensing container (such as the tube) through its dispensing needle. The mixture is poured into the opening of the elongate member until the mixture slightly overflows into the recess (surrounding the opening). Thereafter, the dispensing needle is removed and lifted up from the molding stand.

In one embodiment, the mixture (of the epoxy resin and the ink) is cured for forming the coating on the inner surface of the molded body part. Optionally, the assembly of the molded body part (along with electronic part therein) and the molding stand may be kept in a vacuum box prior to the curing. The curing is performed for hardening the coating. For example, the assembly of molded body part and the molding stand is put into the oven at about 60 degree Celsius for about 40 minutes. Alternatively, the curing is induced with ultra violet (UV) light for hardening the coating of epoxy material. Moreover, the UV curing is performed at ambient conditions, such as room temperature.

In one embodiment the method for manufacturing a wearable electronic device comprises the steps of:

molding a body part using a moldable ceramic material, wherein a mold is such that at least one cavity is formed on an inner surface of the body part, arranging an electronic part in said cavity, and coating the inner surface of the body part by applying an epoxy resin on the surface and curing the resin to form an epoxy coating, including covering the electronic part.

In an embodiment, after the curing of the assembly, the assembly is removed from the oven for allowing the assembly to cool down. For example, the assembly is allowed to cool down for about 5-10 minutes, and thereafter the unassembling of the molded body part from the molding stand is performed. Thereafter, an overflow gate (formed due to fluidic coupling between the molding stand and the cavity of the body part) is cut by sharp knife, when cured epoxy coating is slightly warm in order to achieve smooth surface. This forms the epoxy coating on the inner surface of the molded body part for covering the electronic part, thereby forming the wearable electronic device of the present disclosure.

In one embodiment, the wearable electronic device finally passes through a finishing process. In an example, the finishing process includes visually checking an outlook of molding quality and check whether the charging pads are clean. Finally, the wearable electronic device is subjected to a polishing machine for mainly polishing the outer surface of the molded body part.

The present disclosure provides a wearable electronic device and a method for manufacturing thereof. The present disclosure provides a simple and efficient waterproof construction for a wearable electronic device, such as a ring and a band. Specifically, the wearable electronic device of the present disclosure precludes a need for two-part covers, o-ring and screws for attaining waterproof construction. Further, the wearable electronic device has a smooth inner surface, i.e. free from any depression or elevation, which avoids deposit of dirt on the inner surface. Moreover, the inner surface is provided with the coating of epoxy material, which provides good adherence with user's skin when worn on a finger. Additionally, the coating of epoxy material makes the wearable electronic device hypoallergic, which does not cause skin irritations and allergies when comes in contact with the user's skin.

DETAILED DESCRIPTION OF THE DRAWINGS

Figure 1:
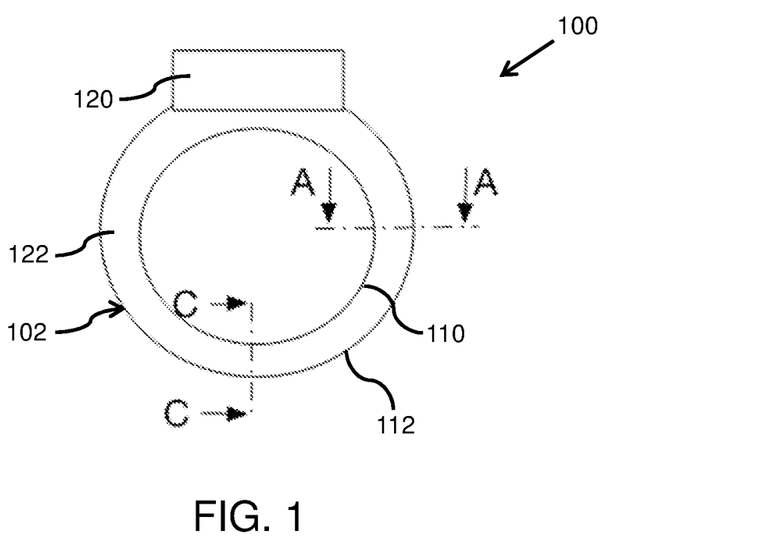
FIG. 1 is a schematic side view of a wearable electronic device, in accordance with an embodiment of the present disclosure.

Referring to FIG. 1, illustrated is a schematic side view of a wearable electronic device 100, in accordance with an embodiment of the present disclosure. The wearable electronic device 100 includes a molded body part 102 made of a moldable ceramic material. As shown, the molded body part 102 is configured to have a shape of ring that can be suitably worn on a finger of a user. The molded body part 102 includes an inner surface 110 and an outer surface 112 opposite to the inner surface 110. The molded body part 102 also includes at least one cavity (shown and explained in conjunction with subsequent figures) having a depth and arranged on the inner surface 110 of the moldable body part 102. Further, as shown, the molded body part 102 includes a central portion 120 and a loop 122 integral with the central portion 120.

Figure 2:
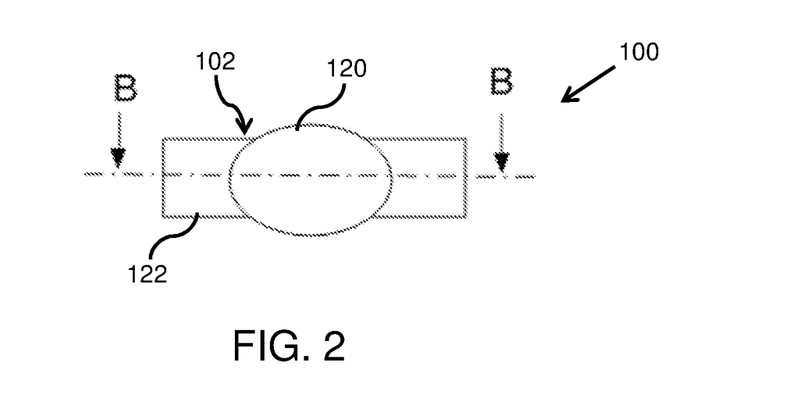
FIG. 2 is a schematic top view of the wearable electronic device, in accordance with an embodiment of the present disclosure.

Referring now to FIG. 2, illustrated is a schematic top view of the wearable electronic device 100, in accordance with an embodiment of the present disclosure. Specifically, FIG. 2 illustrates the molded body part 102, i.e. the central portion 120 and the loop 122 extending from the central portion 120.

Figure 3:
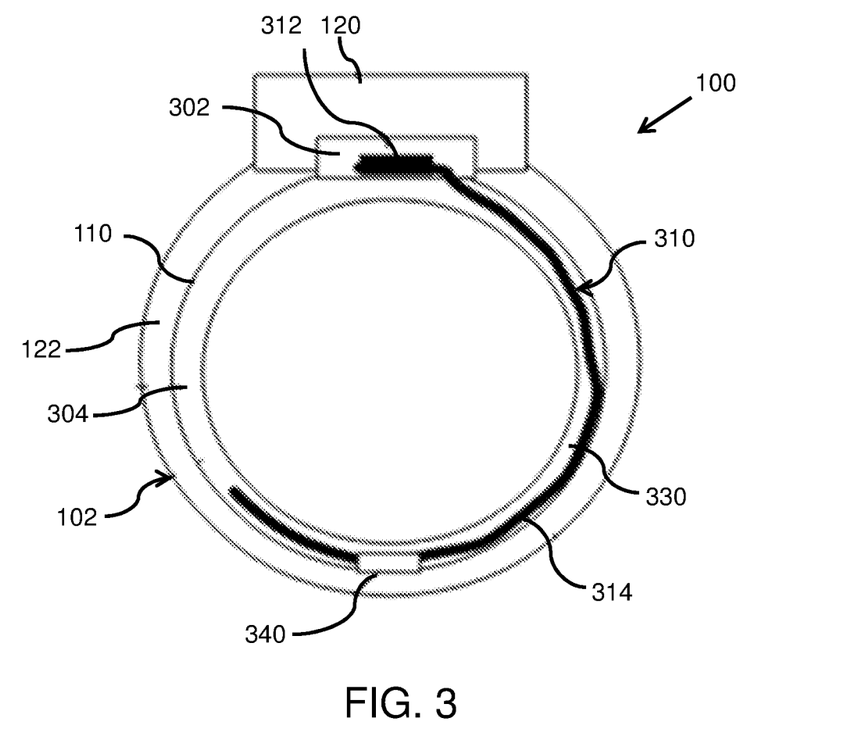
FIG. 3 is a schematic cross-sectional view of the wearable electronic device along an axis B-B of the FIG. 2, in accordance with an embodiment of the present disclosure.

Referring now to FIG. 3, illustrated is a schematic cross-sectional view of the wearable electronic device 100, in accordance with an embodiment of the present disclosure. Specifically, FIG. 3 illustrates the cross-sectional view of the wearable electronic device 100 along the axis B-B of the FIG. 2. As shown, the molded body part 102 includes at least one cavity, particularly, the cavity arranged on the inner surface 110 and running along the central portion 120 and the loop 122. Specifically, the least one cavity includes a first cavity 302 and a second cavity 304 connected to the first cavity 302. The first cavity 302 is configured on the central portion 120 and the second cavity 304 is configured on the loop 122. Further, a depth of the first cavity 302 is configured to be more than a depth of the second cavity 304.

The wearable electronic device 100 further includes an electronic part 310 arranged in the cavity, i.e. in the first cavity 302 and the second cavity 304. Specifically, the electronic part 310 includes a first part 312 and a second part 314. The first part 312 is configured to be received in the first cavity 302 and the second part 314 is configured to be received in the second cavity 304. For example, the first part 312 includes electronic elements such as, a battery and a microcontroller, revived in the first cavity 302. The second part 314 includes a support (a flexible printed circuit board) designed to be received, primarily in the second cavity 304 and marginally in the first cavity 302. Further, the second part 314 includes a plurality of electronic components, which includes but not be limited to an infrared (IR) transmitter, an IR receiver, a microcontroller, a RF (radio frequency) transceiver and a temperature sensor, arranged thereon. The first part 312 and the second part 314 are coupled to each other (for example with electrical wires, not shown). Moreover, the electronic part 310, i.e. the first part 312 and the second part 314, has a thickness that is less than the depth of the first cavity 302 and the second cavity 304.

Specifically, when the first part 312 and the second part 314 are received in the first cavity 302 and the second cavity 304, respectively, still an unfilled space remains in the first cavity 302 and the second cavity 304.

The wearable electronic device 100 includes a coating 330 made of a moldable filler material such as an epoxy material. The coating 330 is arranged on the inner surface 110 of the molded body part 102 for covering the electronic part 310 and the cavity, i.e. the first cavity 302 and the second cavity 304. Specifically, the coating 330 covers the unfilled space that remains in the first cavity 302 and the second cavity 304 after receiving the first part 312 and the second part 314, respectively, therein. Therefore, the coating 330 acts a cover for the electronic part 310 and forms a surface that contacts a skin of the user when the wearable electronic device 100 is worn on the finger.

FIG. 3 also illustrates an assembly guiding element 340 arranged on the inner surface 110 of the loop 122. The assembly guiding element 340 aligns the electronic part 310 in proper position with respect to the molded body part 102. Specifically, the assembly guiding element 340 is a protruded structure adapted to be received by a hole or cavity (not shown) configured on the second part 314 (particularly on the support i.e. flexible printed circuit board) for properly aligning the electronic part 310 with respect to the molded body part 102.

Figure 4:
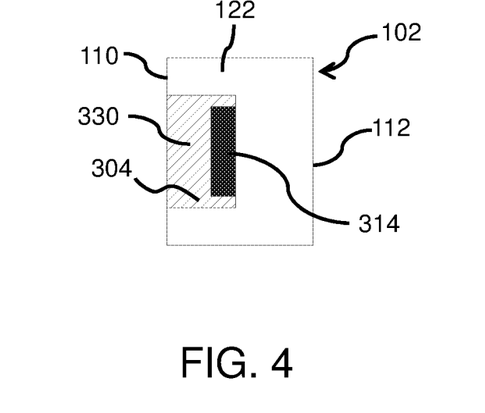
FIGS. 4 and 5 are schematic cross-sectional views of the wearable electronic device of FIG. 1 along axes A-A and C-C, respectively, in accordance with an embodiment of the present disclosure.
Figure 5:
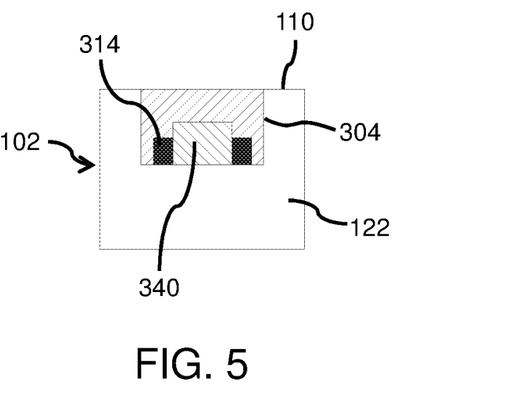

Referring now to FIGS. 4 and 5, illustrated are cross-sectional views of the wearable electronic device 100 (of FIG. 1) along axes A-A and C-C, respectively, in accordance with an embodiment of the present disclosure. Specifically, the FIGS. 4 and 5 illustrate cross-sectional views of the loop 122 of the molded body part 102 along the axes A-A and C-C, respectively. The molded body part 102 includes the outer surface 112, the inner surface 110 and the cavity, particularly, the second cavity 304 for receiving the electronic part, particularly, the second part 314, therein. As shown, the second part 314 sits on the second cavity 304 touching the inner surface 110. Further, the coating 330 is provided on the inner surface 110 of the molded body part 102 for covering the electronic part, particularly, the second part 314.

Further, FIG. 5 illustrates the assembly guiding element 340 aligning the electronic part 310 (shown in FIG. 3) in the cavity of the molded body part 102. Specifically, the second part 314 (particularly the flexible printed circuit board of the electronic part 310) includes a hole (not shown) for receiving the assembly guiding element 340 therethrough for aligning the second part 314 (i.e. electronic part 310) in proper position with respect to the second cavity 304 of the molded body part 102. Further, the second part 314 sits on the second cavity 304 touching the inner surface 110 of the molded body part 102.

Figure 6:
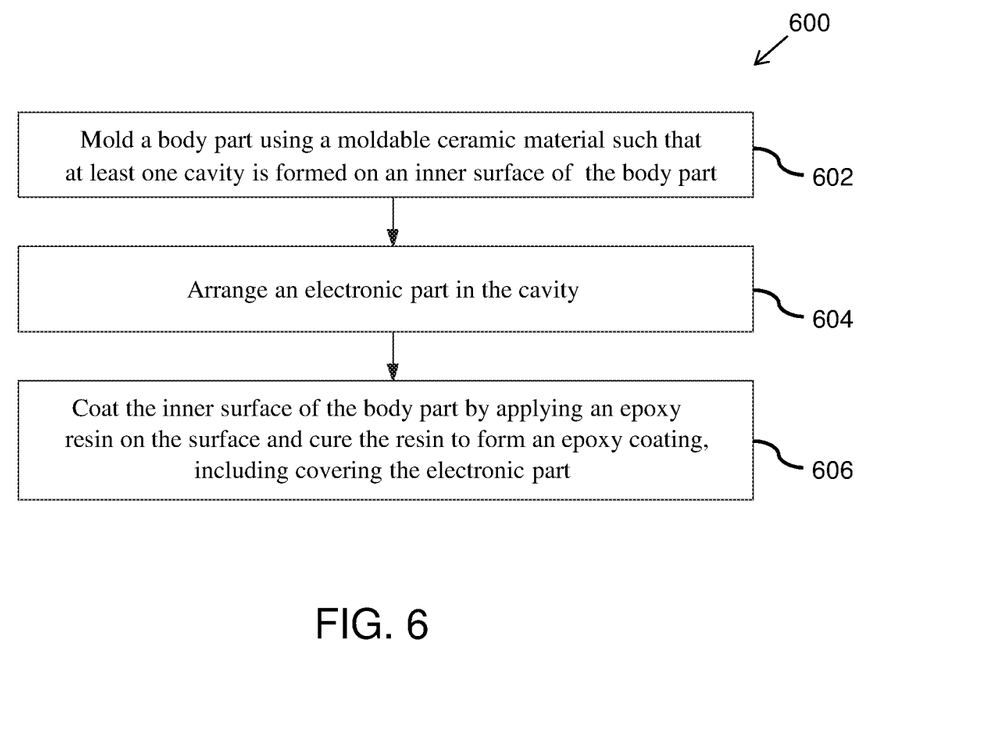
FIG. 6 is an illustration of steps of a method for manufacturing a wearable electronic device, in accordance with an embodiment of the present disclosure.
Figure 7A:
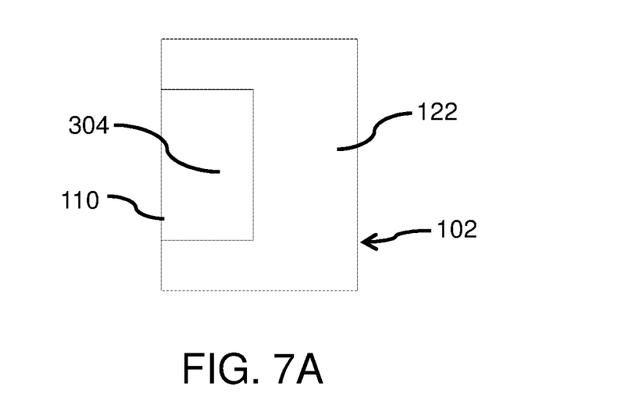
FIGS. 7A-7C illustrate the steps of the method of FIG. 6, in accordance with an embodiment of the present disclosure.
Figure 7B:
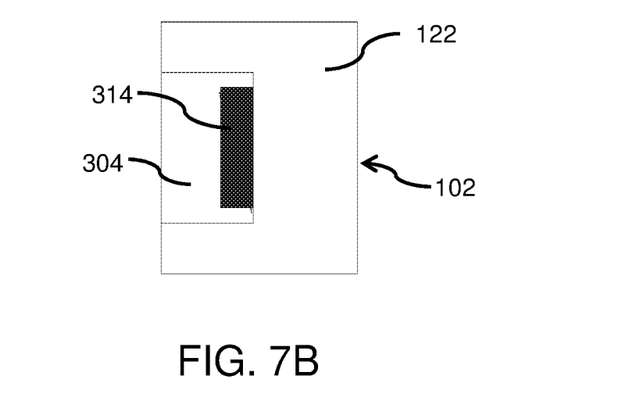
Figure 7C:
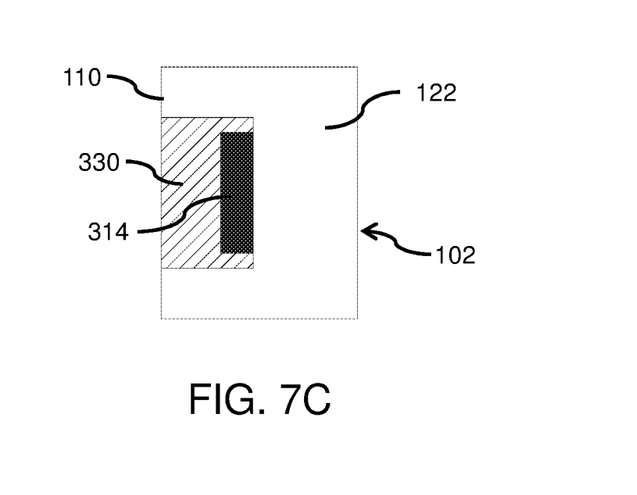

Referring now to FIG. 6, illustrated are steps of a method 600 for manufacturing a wearable electronic device, in accordance with an embodiment of the present disclosure. Specifically, the method 600 illustrates the steps of manufacturing the wearable electronic device 100, explained in conjunction with the FIGS. 1-5.

At step 602, a molded body part is molded using a moldable ceramic material and a mold is such that at least one cavity is formed on an inner surface of the molded body part.

At step 604, an electronic part is arranged in the cavity.

At step 606, the inner surface of the molded body part is applied with a coating of an epoxy resin and epoxy resin is cured to form an epoxy coating for covering the electronic part.

The steps 602 to 606 are only illustrative and other alternatives can also be provided where one or more steps are added, one or more steps are removed, or one or more steps are provided in a different sequence without departing from the scope of the claims herein. For example, the method 600 further includes attachment of the electronic part to the cavity using attachment means arranged on a bottom of the cavity. Further, the method 600 includes arranging the electronic part in the cavity using an assembly guiding element. Moreover, in the method 600 the mold (for the molded body part) is such that two cavities, a first cavity and a second cavity, are formed on the inner surface of the molded body part. Additionally, the first cavity and the second cavity are in connection with each other. Further, in the method 600, arranging the electronic part (which includes a battery and a support on which other components of the electronic part are arranged) in the cavity is carried out by arranging the battery in the first cavity, connecting the battery to the support and arranging the support in the second cavity. Moreover, in the method 600, the curing is induced with UV light. Additionally, in the method 600, the coating of the inner surface of the molded body part is carried out using a molding stand.

The method 600 of the present disclosure is further explained in conjunction with subsequent figures, i.e. FIGS. 7-12. Specifically, the FIGS. 7A-7C illustrate the steps 602-606, respectively, of the method 600 for manufacturing the wearable electronic device 100 (shown in FIG. 1). More specifically, FIGS. 7A-7C illustrate cross-sectional views of the loop 122 of the molded body part 102. Therefore, as mentioned above, FIG. 7A illustrates the molded body part 102 having at least one cavity, particularly the second cavity 304, formed on the inner surface 110 of the loop 122. Further, FIG. 7B illustrates the electronic part 310 (shown in FIG. 3), particularly the second part 314 (the flexible printed circuit board) arranged in the cavity, such as the second cavity 304. Moreover, FIG. 7C illustrates the inner surface 110 of the molded body part 102 applied with a layer of an epoxy resin being cured to form the coating 330 for covering the electronic part, such as the second part 314 thereof. It is to be understood that if FIGS. 7A-7C would have illustrated cross-sectional views of the central portion 120 (shown in FIG. 3) of the molded body part 102, in such instance FIGS. 7A-7C would have been explained in conjunction with the first part 312 (shown in FIG. 3) of the electronic part 310 and the first cavity 302.

Figure 8:
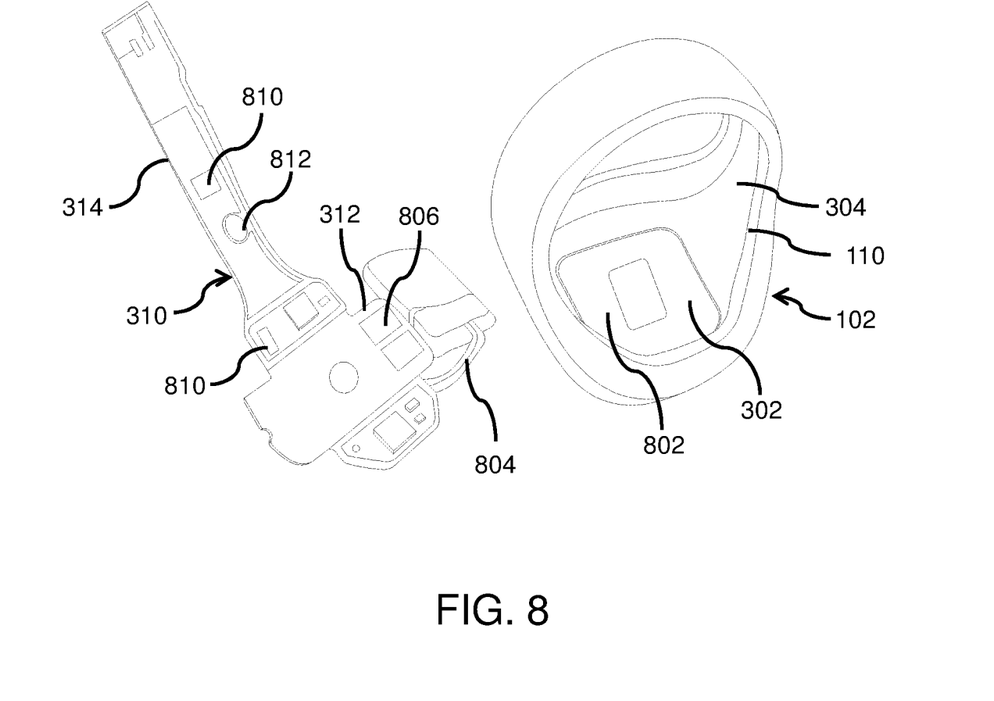
FIG. 8 is a perspective view of a molded body part and an electronic part of the wearable electronic device in an unassembled state, in accordance with an embodiment of the present disclosure.

Referring now to FIG. 8, illustrated is a perspective view of the molded body part 102 and the electronic part 310 of the wearable electronic device 100 (as shown in FIG. 1) in an unassembled state, in accordance with an embodiment of the present disclosure. As mentioned above, the molded body part 102 is made of a moldable ceramic material using a mold (not shown) such that two cavities, the first cavity 302 and the second cavity 304, are formed on the inner surface 110 of the molded body part 102. Further, the first cavity 302 and the second cavity 304 are in connection with each other. Moreover, as mentioned above, the attachment of the electronic part 310 to the cavity (i.e. the first cavity 302 and the second cavity 304) uses attachment means arranged on a bottom of the cavity. As shown, a stick foam tape 802 (i.e. attachment means) is arranged on the first cavity 302. Similarly, another stick foam tape (not shown) may be arranged on the second cavity 304 (or on the electronic part 310).

As shown in FIG. 8, the electronic part 310 includes the first part 312 (such as a battery and a portion of the support mounted with a microcontroller and the second part 314

(such as the support i.e. flexible PCB) connected to the first part 312. For example, the first part 312 is connected to the second part 314, i.e. the battery is connected to the support using a wire 804. The first part 312 also includes charging pads 806 for charging the battery. Further, on the second part 314, i.e. the support, other components 810 of the electronic part 310 are arranged. For example, the other components 810 include but are not limited to IR transmitter, the IR receiver, the microcontroller, the RF transceiver and the temperature sensor. The second part 314 also includes a hole 812 for aligning the second part 314 with the molded body part 102.

Figure 9:
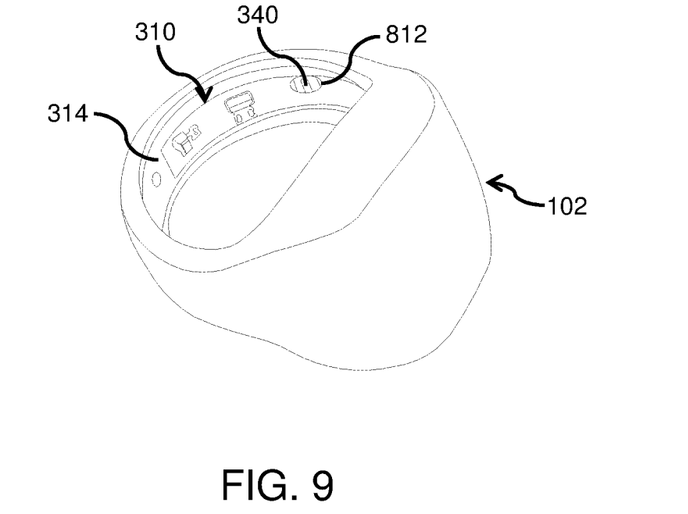
FIG. 9 is a perspective view of the molded body part and the electronic part in an assembled state, in accordance with an embodiment of the present disclosure.

Referring now to FIG. 9, associated with the step of arranging the electronic part 310 in the cavity, i.e. by arranging the battery and the portion of the support mounted with the microcontroller in the first cavity 302 (shown in FIG. 8) and arranging the support (with other electronic elements arranged thereon) in the second cavity 304 (shown in FIG. 8). Specifically, FIG. 9 illustrates a perspective view of the molded body part 102 and the electronic part 310 in an assembled state. The first part 312 (as shown in FIG. 8) and the second part 314 are of the electronic part 310 received in the first and second cavities, 302,304 (shown in FIG. 8) respectively, and thereafter the first part 312 and the second part 314 are pressed to couple with the molded body part 102 with the help of the attachment means, such as the stick foam tape 802 (shown in FIG. 8). As mentioned above, the step of arranging the electronic part 310 in the cavity is carried out using the assembly guiding element 340. Specifically, the hole 812 arranged in the second part 314 of the electronic part 310 receives the assembly guiding element 340 therethrough for aligning the electronic part 310 in proper position with respect to the molded body part 102.

Figure 10:
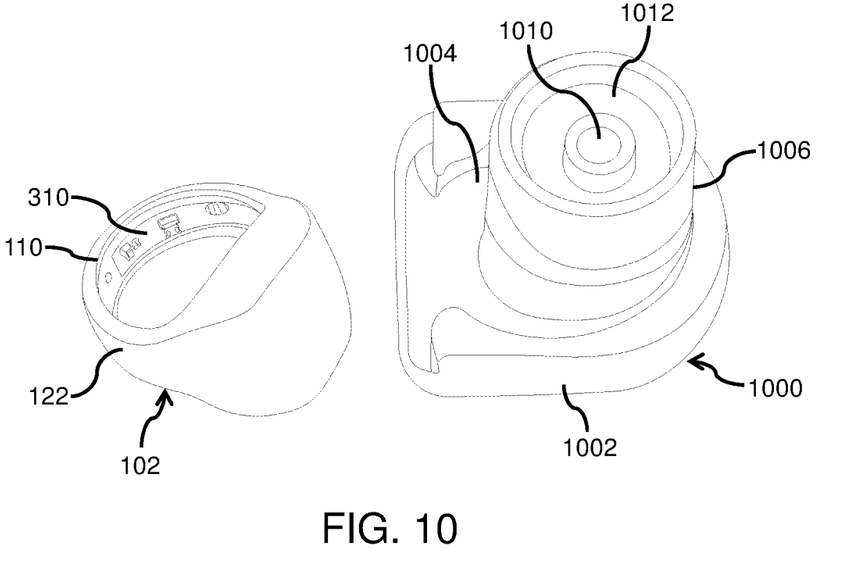
FIG. 10 is a perspective view of the assembled molded body part and the electronic part, and a molding stand positioned adjacent thereto, in accordance with an embodiment of the present disclosure.

Referring now to FIG. 10, associated with the step of coating the inner surface 110 of the body part 102 that is carried out using a molding stand 1000. Specifically, FIG. 10 illustrates a perspective view of the assembled molded body part 102 and the electronic part 310, and the molding stand 1000 positioned adjacent thereto. The molding stand 1000 includes a base 1002, a channel 1004 configured on the base 1002 and an elongate member 1006 extending from the base 1002. The channel 1004 and the elongate member 1006 are configured to conform to a shape of the molded body part 102. Specifically, the channel 1004 is configured to conform to a thickness of the molded body part 102, whereas the elongate member 1006 is configured to conform to a circumference (or diameter) of the loop 122 of the molded body part 102. This allows the molded body part 102 to firmly fit over the elongate member 1006 of the molding stand 1000. The elongate member 1006 further includes an opening 1010 and a recess 1012 surrounding the opening 1010.

Figure 11:
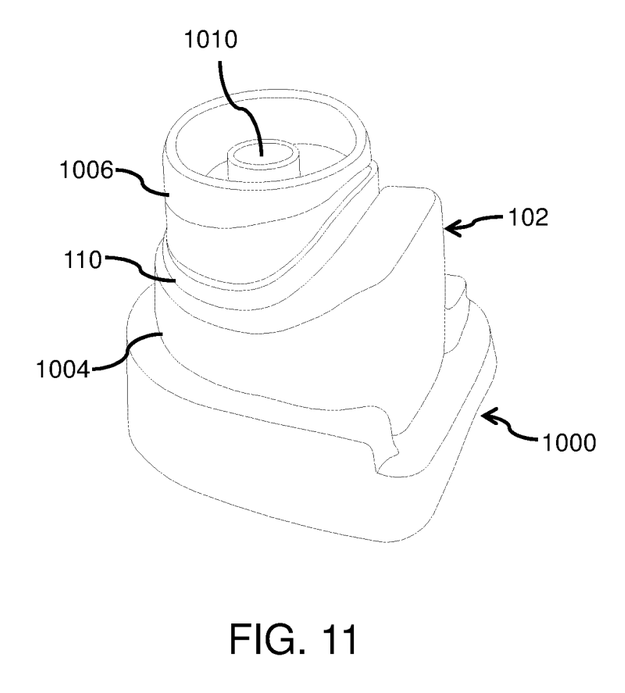
FIG. 11 is a perspective view of the molded body part, arranged with the electronic part, mounted on the molding stand, in accordance with an embodiment of the present disclosure.
Figure 12:
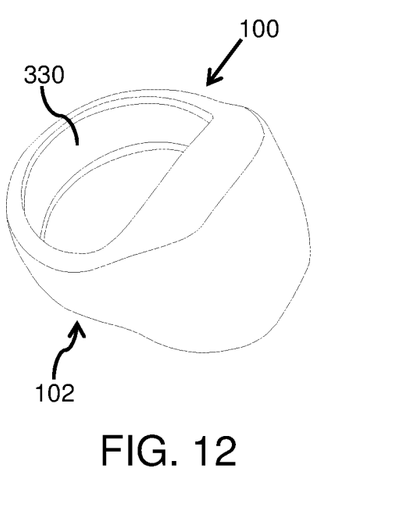
FIG. 12 is a perspective view of the wearable electronic device, in accordance with an embodiment of the present disclosure.

Referring now to FIG. 11, illustrated is a perspective view of the molded body part 102 (arranged with the electronic part therein) mounted on the molding stand 1000, in accordance with an embodiment of the present disclosure. Specifically, the channel 1004 and the elongate member 1006 receive the molded body part 102. In such instance, molten epoxy is poured through the opening 1010 for being received by the cavity (particularly the unfilled space remains in the first cavity 302 and the second cavity 304 after receiving the electronic part 310 therein, as shown in FIG. 9). This allows the formation of an epoxy coating on the inner surface 110 of the molded body part 102 for covering the electronic part and the cavity, as shown in FIG. 12. Specifically, the FIG. 12 illustrates a perspective view of the wearable electronic device 100 having the molded body part 102, the electronic part 310 (shown in FIG. 9) arranged in the molded body part 102 and the coating 330 covering the electronic part 310.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A wearable electronic device comprising:
   a body part made of a non-ceramic material, having an inner surface and an outer surface, wherein at least one cavity is formed on the inner surface of the body part, the at least one cavity extending from the inner surface of the body part towards the outer surface of the body part and having a depth arranged within the inner surface of the body part,
   an electronic part arranged in said at least one cavity, which electronic part has a thickness that is less than the depth of the at least one cavity, and
   a coating made of a moldable filler material on the inner surface of the body part, covering the electronic part and the at least one cavity.

2. The wearable electronic device according to claim 1, wherein the non-ceramic material is a titanium material.

3. The wearable electronic device according to claim 1, wherein the non-ceramic material is a machinable material.

4. The wearable electronic device according to claim 1, wherein the non-ceramic material is a machinable titanium material.

5. The wearable device according to claim 1 wherein the non-ceramic material is a machinable metallic material comprising one or more of titanium, steel, platinum, gold, palladium, silver or bronze or a gold based alloys.

6. The wearable electronic device according to claim 1, wherein the electronic part is attached to the cavity a bottom of the cavity.

7. The wearable electronic device according to claim 6, comprising one or more of a sticker, a tape or glue that attaches the electronic part to the at least one cavity at a bottom of the at least one cavity.

8. The wearable electronic device according to claim 1, wherein the moldable filler material is selected from a group consisting of at least epoxy material, Polyethylene, Polyurethane, low temperature moldable material, Loctite M-31CL, alpha-epoxy, 1,2-epoxy, EpoxAcast® 650, Bisphenol S epoxy resin, Novolac epoxy resin, Aliphatic epoxy resin and Glycidylamine epoxy resin.

9. The wearable electronic device according to claim 1, wherein the electronic part comprises one or more of a battery, an infrared transmitter, a microcontroller, a radio frequency transceiver, a temperature sensor and an infrared receiver.

10. The wearable electronic device according to claim 9, wherein the moldable filler material comprises an ink and is configured to cover at least an area other than the infrared transmitter and the infrared receiver within the at least one cavity.

11. The wearable electronic device according to claim 1, wherein the moldable filler material comprises an ink that increases a value of transmitted infrared light intensity divided by transmitted visible light intensity.

12. The wearable electronic device according to claim 1, wherein the body part comprises a ring configured to be worn on a finger.

* * * * *

Disclaimer

10,893,833 B2 - Teemu Haverinen, Oulu (FI); Marko Kelloniemi, Oulu (FI); Tomi Hautala, Oulu (FI); Markku Koskela, Oulu (FI); Kari Kivalä, Helsinki (FI); WEARABLE ELECTRONIC DEVICE AND METHOD FOR MANUFACTURING THEREOF. Patent dated December 29, 2020. Disclaimer filed September 12, 2024, by the assignee, Oura Health Oy.

I hereby disclaim the following complete Claims 1-12 of said patent.

*(Official Gazette, December 10, 2024)*